United States Patent [19]
Mori et al.

[11] Patent Number: 5,118,833
[45] Date of Patent: Jun. 2, 1992

[54] PROCESS FOR PRODUCING ALPHA-KETO-CARBOXYLIC ACID ESTER

[75] Inventors: Toshiki Mori, Kurashiki, Japan; Shigeaki Suzuki, Mountain View, Calif.; Takashi Onishi; Kazuo Yamamoto, both of Kurashiki, Japan

[73] Assignee: Kuraray Company, Ltd., Kurashiki, Japan

[21] Appl. No.: 537,647

[22] Filed: Jun. 14, 1990

[30] Foreign Application Priority Data

Jul. 28, 1989 [JP] Japan .................................. 1-197109

[51] Int. Cl.$^5$ ...................... C07C 69/76; C07C 69/74; C07C 69/66
[52] U.S. Cl. ..................... 560/51; 560/126; 560/174
[58] Field of Search ................... 560/174, 126, 51

[56] References Cited
FOREIGN PATENT DOCUMENTS 140454 5/1985 European Pat. Off. .
316783 5/1989 European Pat. Off. .

OTHER PUBLICATIONS

Journal of Organic Chemistry vol. 52, no. 12, 12 Jun. 1987, pp. 2559–2562, American Chemical Society, Washington, DC, US; P. N. Anelli et al.: "Fast and Selective Oxidation of Primary Alcohols to Aldehydes or to Carboxylic Acids and of Secondary Alcohols to Ketones Mediated by Oxoamminium Salts under Two-Phase Conditions" *The whole article*.

*Primary Examiner*—Paul J. Killos
*Attorney, Agent, or Firm*—Oblon, Spivak, McClelland, Maier & Neustadt

[57] ABSTRACT

The invention provides a novel process for produing α-keto-carboxylic acid esters that are useful as intermediates for the preparation of pharmaceutical drugs in high yield by oxidizing α-hydroxycarbocylic acid esters with hypochlorous acid in the presence of nitroxy radical.

6 Claims, No Drawings

PROCESS FOR PRODUCING ALPHA-KETO-CARBOXYLIC ACID ESTER

BACKGROUND OF THE INVENTION

1. Field of the Invention

This invention relates to a process producing α-keto-carboxylic acid ester of the general formula (1),

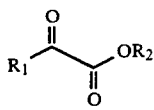
(1)

wherein $R_1$ represents an alkyl group, a cycloalkyl group, an aryl group or an aralkyl group having four or more carbon atoms and $R_2$ represents a lower alkyl group.

The α-keto-carboxylic acid esters of the general formula (1) produced according to the process of the invention are useful as intermediates for preparing pharmaceutical drugs.

2. Description of the Related Art

Previously, α-keto-carboxylic acid esters are known as prepared, for example, according to the following processes.

(1) Process by oxidizing reaction of α-hydroxycarboxylic acid esters

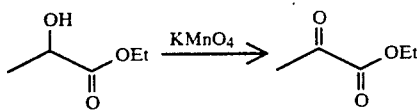

J. W. Conforth, Org. Syn. coll. Vol. 4, 467 (1963).

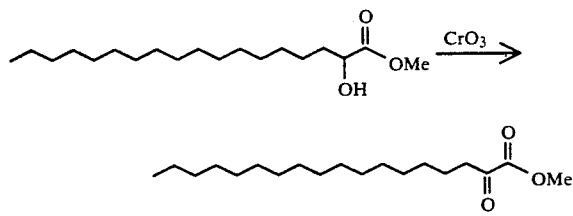

S. Bergstrom, et al., Acta Chem. Scand., 6, 1157 (1952).

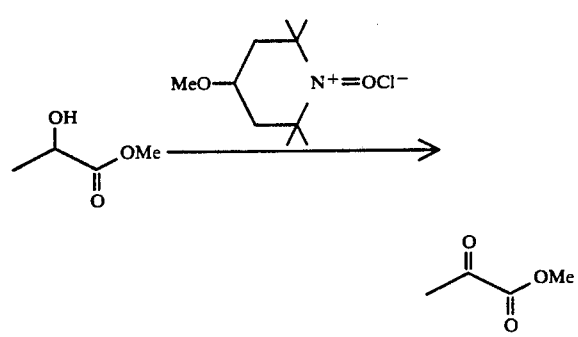

T. Miyazawa, et al., J. Org. Chem., 50, 1332 (1985).

(2) Process by esterifying reaction of α-keto-carboxylic acid

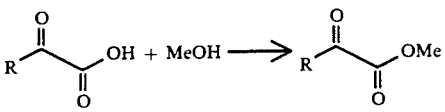

A. Weissberger, et al., Org. Syn. coll. Vol. 3, 610 (1943).

Also α-keto-carboxylic acid is known as prepared according to the following method.

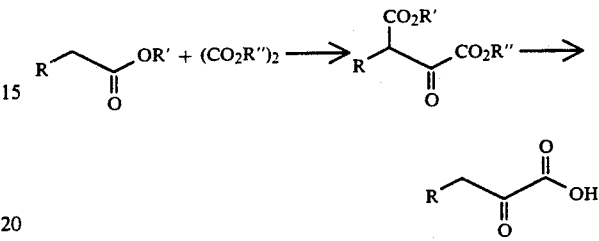

Adickes, et al., Ann., 555, 41 (1943).

(3) Process by Grignard's reaction

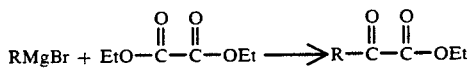

L. M. Weinstock, et al., Synthetic Commun., 11 (12), 943 (1981).

These aforementioned prior art processes of preparing α-keto-carboxylic acid esters have had following problems. In the process of using readily available α-hydroxycarboxylic acid as a starting material, the use of a toxic reagents such as potassium permanganate or chromic acid, or the use of an expensive reagent such as oxoaminium salt and the like in an amount of one or more equivalents are required. In the process of esterifying α-keto-carboxylic acid, α-keto-carboxylic acid is not generally readily available because of a long reaction sequence for preparation. In the process of using Grignard's reaction, it has a problem of in low yield.

Therefore, the object of the present invention is to provide a process for producing α-keto-carboxylic acid esters from an inexpensive and readily available α-hydroxycarboxylic acid ester.

SUMMARY OF THE INVENTION

According to the invention, the above-mentioned object can be accomplished by a process of producing α-keto-carboxylic acid esters of the general formula (1),

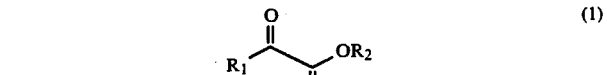
(1)

wherein $R_1$ represents an alkyl group, a cycloalkyl group, a substituted or unsubstituted aryl group or an aralkyl group having four or more carbon atoms, and $R_2$ represents a lower alkyl group, which comprises oxidizing α-hydroxycarboxylic acid ester of the general formula (2),

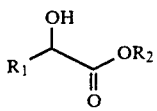

(2)

wherein $R_1$ and $R_2$ represent as defined above, with hypodrochlorous acid in the presence of nitroxy radical of the general formula (3),

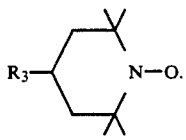

(3)

wherein $R_3$ represents a hydrogen atom, an acyloxy group, an alkoxy group or an aralkyloxy group.

DESCRIPTION OF THE PREFERRED EMBODIMENTS $R_1$, $R_2$ and $R_3$ in the aforementioned general formulas are described in detail.

In the definition of $R_1$, the upper limit of the carbon number of alkyl group is not particularly set, but the carbon number is normally from four to twelve from the practical standpoint.

Examples of the alkyl group having from four or more carbon atoms include a n-butyl group, n-pentyl group, a n-hexyl group, a n-heptyl group, a n-octyl group, a n-decyl group, a n-dodecyl group, a sec-butyl group, a tert-butyl group, a neopentyl group, a iso-octyl group and the like.

In the definition of $R_1$, examples of the cycloalkyl group include a cyclopentyl group, a cyclohexyl group and the like.

In the definition of $R_1$, examples of the substituted or unsubstituted aryl group include a phenyl group or a phenyl group having one or two or more substituents selected from the group consisting of a methoxy group, a chlorine atom, a bromine atom, a fluorine atom, an iodine atom, a methyl group, an ethyl group, a propyl group or the like at any positions of ortho-, meta- or para-position.

In the definition of $R_1$, examples of the aralkyl group include a benzyl group, a phenylethyl group, a 3-phenylpropyl group, a 2-phenylpropyl group, a p-methylphenylethyl group and the like.

Examples of the lower alkyl group of $R_2$ usually include an alkyl group having from one to five carbon atoms such as a methyl group, an ethyl group, a n-propyl group, a n-butyl group, a n-pentyl group, an isopropyl group, a sec-butyl group, a tert-butyl group and a neopentyl group.

Examples of α-hydroxcarboxylic acid ester of the general formula (2) include 2-hydroxyvaleric acid methyl ester, 2-hydroxyvaleric acid ethyl ester, 2-hydroxycaproic acid methyl ester, 2-hydroxycaproic acid ethyl ester, mandelic acid methyl ester, mandelic acid ethyl ester, 2-hydroxy-4-phenylbutyric acid methyl ester, 2-hydroxy-4-phenylbutyric acid ethyl ester 2-hydroxy-4-p-tolybutyric acid ethyl ester and the like.

$R_3$ represents a hydrogen atom, an acyloxy group, an alkoxy group or an aralkyloxy group. Examples of the acyloxy group include an acetoxy group, an propionyloxy group, a benzoyloxy group and the like. Examples of the alkoxygroup include a methoxy group, an ethoxy group and the like. Examples of the aralkyloxy group include a benzyloxy group and the like.

Examples of the nitroxy radical of the general formula (3) include a 2,2,6,6-tetramethylpiperidinyl-1-oxy radical, a 4-acetoxy-2,2,6,6-tetramethylpiperidinyl-1-oxy radical, a 4-methoxy-2,2,6,6-tetramethylpiperidinyl-1-oxy radical, a 4-benzyloxy-2,2,6,6-tetramethylpiperidinyl-1-oxy radical and the like.

The amount of the nixtroxy radical of the general formula (3) used in the reaction is in the range of from about 0.05 to about 10 mole percent, preferably from about 0.1 to about 0.5 mole percent from the standpoint of reactivity and economics based on the amount of α-hydroxycarboxylic acid ester of the general formula (2).

The hypochlorous acid effecting in the reaction is generated in the reaction system from salts of hypochlorous acid such as sodium hypochorite, potassium hypochlorite and bleaching powder.

Examples of the reagents generating hypochlorous acid from salts of hypochlorous acid include hydrogen carbonates such as sodium hydrogen carbonate and potassium hydrogen carbonate; mineral acids such as hydrochloric acid, sulfuric acid, nitric acid, boric acid and phosphoric acid; organic acids such as acetic acid, propionic acid and tosylic acid; potassium dihydrogen phosphate, sodium dihydrogen phosphate, potassium hydrogen phthalate and the like.

The amount of hypochlorous acid used in the reaction is satisfactorily one or more equivalents, preferably from about 1.1 to about 1.3 equivalents to the amount of α-hydroxycarboxylic acid ester of the general formula (2) from the standpoint of efficient reaction proceeding.

Further, among these salts of hypochlorous acid, sodium hypochorite is most preferably because of inexpensiveness, easy availability in large amount and easy-handling of its commercially available aqueous solution form. When sodium hypochlorite is used, commercially available sodium hypochlorite aqueous solution having a concentration of 12 to 13 percent can be used as such or diluted to an easy-to-control concentration. When a solid substance such as bleaching powder is used, it is preferable to dissolve or to suspend in water forming an aqueous solution or aqueous suspended solution having a concentration of from about 5 to about 20%.

Moreover the amount of the reagent generating hypochlorous acid from a salt of hypochlorous acid is also a key factor. When the amount of the reagent is less than the preferrable range, side reactions occur resulting in the decrease of the objective α-keto-carboxylic acid ester in yield. When the amount of the reagent is more than the preferable range, a large amount of hypochlorous acid occurs at a time which causes not only the difficulty in the removal of the generated heat, but also the existing of thermally unstable and liable-to-decompose hypochlorous acid in excess, which is the most unfavorable state in commercial production scale.

Therefore, the amount of the reagent to generate hypochlorous acid from a salt of hypochlorous acid is in the range of from 5 to 25 mole percent to the amount of a salt of hypochlorous acid. Among these reagents, sodium hydrogen carbonate, hydorchloric acid, sulfuric acid and the like are the most favorable reagents for the reaction because of the readily availablity and inexpensiveness. The reagent is preferably added to the reaction system just before the reaction commencement, in the case of solid state, as such or dissolved in water, and in the case of liuqid state, as such or diluted by water.

The reaction is carried out at a temperature ranging from 0° C. to 30° C., perferably from 0° C. to 15° C. considering the stability of hypochlorous acid.

The reaction is preferably effected in an organic solvent, more preferably in a halogenated hydrocarbon solvent such as dichloromethane, chloroform, carbon tetrachloride and 1,2-dichloroethane, in an amount of from 1 to 10 times by weight based on the amount of α-hydroxycarboxylic acid ester.

The reaction has been completed in a period of from about 10 minutes to about 5 hours depending on the reaction temperature and the amount of nitroxy radical used.

After the treatment of excessive hypochlorous acid with sodium thiosulfate and the like, the reaction mixture is subjected to separation. Further the organic phase is washed with water or sodium carbonate aqueous solution or the like, thereafter the organaic solvent is removed. The obtained α-keto-carboxylic acid ester is subjected to a pruification procedure such as distillation, column chromatography or the like.

EXAMPLES

The present invention is more particularly described by way of examples, which should not be construed as limiting the invention.

EXAMPLE 1

Preparation of 2-Keto-4-Phenylbutyric Acid Ethyl Ester Using Sodium Hypochlorite and Sodium Hydrogen Carbonate A 500 ml flask was charged a solution dissolving 41.6 g (200 mmol) of 2-hydroxy-4-phenylbutyric acid ethyl ester in methylene chloride (100 ml) and 148.8 g (purity 12%, 240 mmol) of sodium hypochlorite, and cooled at 5° C. To the reaction mixture was added 86 mg (0.4 mmol) of 4-acetoxy-2,2,6,6-tetramethylpiperidinyl-1-oxy and further added 3.02 g (36 mmol) of sodium hydrogen carbonate. The gradual exothermal reaction proceeded, and the starting material of 2-hydorxy-4-phenylbutyric acid ethyl ester was disappeared in 1.5 hours. The reaction was terminated by adding 100 ml of 5% sodium thiosulfate aqueous solution and was separated. The organic phase was washed with 50 ml of 5% sodium thiosulfate aqueous solution and then 100 ml of 1% sodium carbonate aqueous solution, followed by the removal of the solvent by a rotary evaporator. The residue was subjected to distillation under reduced pressure to obtain 40 g of 2-keto-4-phenylbutyric acid ethyl ester having a boiling point of 103° C. at 0.3 mmHg. The yield was 92%.

EXAMPLE 2

Preparation of 2-Keto-4-Phenylbutyric Acid Ethyl Ester Using Soidium Hypochlorite and Hydrochloric Acid A 200 ml flask was charged with a solution dissolving 20.8 g (100 mmol) of 2-hydroxy-4-phenylbutyric acid ethyl ester in methylene chloride (50 ml) and 72.6 g (purity 12.3%, 120 mmol) of sodium hypochlorite, and cooled at 6° C. To the reaction mixture was added 43 mg (0.2 mmol) of 4-acetoxy-2,2,6,6-tetramethylpiperidinyl-1-oxy and further added 10 ml (10 mmol) of 1N hydrochloric acid. The gradual exothermal reaction proceeded, and the starting material of 2-hydroxy-4-phenylbutyric acid ethyl ester was disappeared in 30 minutes. After the reaction was stopped by adding 10 ml of 5% sodium thiosulfate aqueous solution, the reaction mixture was subjected to the after treatment as described in Example 1 to obtain 18.55 g of 2-keto-4-phenylbutyric acid ethyl ester. The yield was 90%.

EXAMPLE 3

Preparation of 2-Keto-4-Phenylbutyric Acid Ethyl Ester Using Sodium Hypochlorite and Sulfuric Acid According to the same procedure as described in Example 2, using 20.8 g (100 mmol) of 2-hydroxy-4-phenylbutyric acid ethyl ester, methylene chloride (50 ml), 72.6 g (purity 12.3%, 120 mmol) of sodium hypochlorite, 43 mg (0.2 mmol) of 4-acetoxy-2,2,6,6-tetramethylpiperidinyl-1-oxy, and 10 ml (10 mmol) of 1N sulfuric acid, was obtained 18.95 g of 2-keto-4-phenylbutyric acid ethyl ester. The yield was 92%.

EXAMPLE 4, 5 and 6

According to the same procedure as described in Example 1, α-keto-carboxylic acid esters were prepared from corresponding α-hydroxycarboxylic acid ethyl ester. The test results are shown in the following table.

TABLE

| Example Number | α-hydroxycarboxylic acid ethyl ester | α-keto-carboxylic acid ethyl ester | Yield (%) |
|---|---|---|---|
| 4 | -C(=O)-OMe) | -C(=O)-OMe) | 91 |
| 5 | -C(=O)-OEt) | -C(=O)-OEt) | 88 |
| 6 | -C(=O)-OMe) | -C(=O)-OMe) | 95 |

What is claimed is:

1. A process for producing α-keto-carboxylic acid esters of the formula (1),

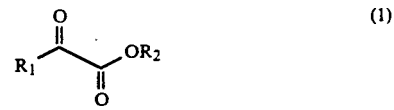

(1)

wherein $R_1$ represents an alkyl group, a cycloalkyl group, a substituted or unsubstituted aryl group or an aralkyl group having four or more carbon atoms, and $R_2$ represents a lower alkyl group, which comprises oxidizing α-hydroxy-carboxylic acid esters of the formula (2),

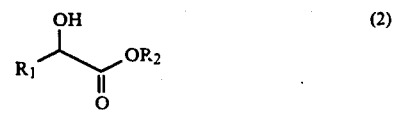

(2)

wherein $R_1$ and $R_2$ are as defined above, with hypochlorous acid in the presence of a nitroxy radical of the formula (3),

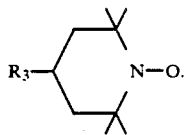
(3)

wherein $R_3$ represents a hydrogen atom, an acyloxy group, an alkoxy group or an aralkyloxy group and wherein the said nitroxy radical is used in an amount of from 0.05 to 10 mole percent relative to the amount of α-hydroxy-carboxylic acid ester.

2. A process according to claim 1, wherein the nitroxy radical of the general formula (3) is used in an amount of from 0.1 to 0.5 mole percent to the amount of α-hydroxycarboxylic acid ester of the general formula (2).

3. A process according to claim 1, wherein the hypochlorous acid is used in an amount of one or more equivalents to the amount of α-hydroxycarboxylic acid ester of the general formula (2).

4. A process according to claim 3, wherein the hydrochlorous acid is used in an amount of from 1.1 to 1.3 equivalents to the amount of α-hydroxycarboxylic acid ester of the general formula (2).

5. A process according to claim 1, wherein the reaction is carried out at a temperature in the range of from 0° C. to 30° C.

6. A process according to claim 5, wherein the reaction is carried out at a temperature in the range of from 0° C. to 15° C.

* * * * *